United States Patent [19]

Eichenberger et al.

[11] 4,053,617

[45] Oct. 11, 1977

[54] 2,1,3-BENZOTHIADIAZOLES AS MYOLONOLYTICS

[75] Inventors: Erwin Eichenberger, Gumligen; Peter Neumann, Berne, both of Switzerland

[73] Assignee: Sandoz Ltd., Basel, Switzerland

[21] Appl. No.: 708,621

[22] Filed: July 26, 1976

[30] Foreign Application Priority Data

July 28, 1975 United Kingdom ............... 31585/75

[51] Int. Cl.$^2$ ........................................... A61K 31/425
[52] U.S. Cl. .................................................... 424/270

[58] Field of Search ........................................ 424/270

[56] References Cited

U.S. PATENT DOCUMENTS 3,843,668   10/1974   Neumann ............................. 424/270

*Primary Examiner*—Stanley J. Friedman
*Attorney, Agent, or Firm*—Gerald D. Sharkin; Robert S. Honor; Thomas O. McGovern

[57] ABSTRACT

This invention provides a new myotonolytic use of 2,1,3-benzothiadiazole derivatives and novel pharmaceutical compositions for such use.

16 Claims, No Drawings

2,1,3-BENZOTHIADIAZOLES AS MYOLONOLYTICS

This invention concerns a novel pharmaceutical activity of 2,1,3-benzothiadiazole derivatives of the formula I,

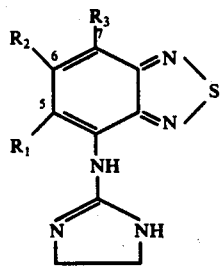

wherein each of $R_1$, $R_2$ and $R_3$, independently, is hydrogen, halogen, alkyl, alkoxy, nitro, cyano, hydroxy or alkylthio,
and novel pharmaceutical compositions containing such compounds of formula I as an active ingredient.

Such compounds are known and are disclosed in U.S. Pat. No. 3,843,668, wherein the compounds are stated to be anti-tremor and anti-rigor agents as indicated by an inhibition of the tremor induced by 2,6-dichlorophenyl acetimidoylureide and by an inhibition of the tremor induced by Thalamonal. It is to be appreciated that the present novel pharmaceutical activity does not extend to the use of the compounds of formula I as such anti-rigor and/or anti-tremor agents.

Preferred compounds of formula I are in general those indicated as preferred in U.S. Pat. No. 3,843,668. Preferably one of $R_1$, $R_2$ and $R_3$ is hydrogen and especially $R_2$ is hydrogen. Preferably one of $R_1$, $R_2$ and $R_3$ is other than hydrogen. Preferred examples include those compounds wherein $R_1$ is chlorine, e.g. 5-chloro-7-methyl-4-(2-imidazolin-2-yl-amino)-2,1,3-benzothiadiazole and especially 5-chloro-4-(2-imidazolin-2-ylamino)-2,1,3-benzothiadiazole.

The compounds have now been found to be useful as myotonolytics, for example for the treatment of spastic conditions of different etiology (neurological, inflammatory, rheumatic, etc.) and muscle relaxants, as indicated by standard tests. For example, in rabbits on i.v. administration of from 0.001 to 0.1 mg/kg animal body weight of the compounds a significant muscle relaxing effect is observed in accordance with the method of Teschendorf et al., Arch. Exp. Pharmacol. 266, 467–468 (1970).

For the above mentioned novel uses the dosage will, of course, vary depending on the compound employed, mode of administration and therapy desired. However, in general, satisfactory results are obtained with a daily dosage of from 0.001 mg to about 1 mg per kg animal body weight, conveniently given in divided doses two to four times a day or in sustained release form. For the larger mammal, the total daily dosage is in the range from about 1 to about 10 mg, e.g. between 1 and 6, preferably between 1.5 and 3 mg.

However, it is especially preferred to use a pharmaceutical composition in unit dosage form comprising from 0.25 mg to 2 mg of a free base form of a compound of formula I as defined above or an equivalent amount of a pharmaceutically acceptable acid addition salt form thereof, in association with a pharmaceutical carrier or diluent. Preferably the unit dosage form contains up to 1.8 mg, preferably up to 1.5 mg of the free base of a compound of formula I or the equivalent amount of pharmaceutically acceptable acid addition salt.

As used herein the term "unit dosage form" refers both to solid and liquid dosage forms and refers generally to that quantity of composition in the final dosage form in question (i.e. compositions as administered), which is appropriate for administration of the required dosage of a compound of formula I.

The compositions may already be in the final form ready for administration, for example in the form of integral solid dosage forms, e.g. a tablet. The composition may be packaged to facilitate administration of a unit dosge form, e.g. an ampoule containing a sterile injectable liquid. In the case of such forms the term "unit dosage form" refers to the weight of compound of formula I in one such form and this, for example, may vary depending on the form in question.

The compositions may contain multiple unit dosages. For example a tablet may be formulated with a break line such that it may be broken into two halves. In such cases the term "unit dosage form" refers to the weight of compound of formula I in any portion thereof, adapted to be separated before administration.

The compositions may be in bulk form, e.g. when in the form of a liquid, a powder, or granules. Such forms may contain the compound of formula I in such a concentration that a conveniently administered portion recognized in the art, e.g. from 1 to 10 ml, e.g. a teaspoonful, contains the required dosage of compound of formula I. In such cases the term "unit dosage form" refers to the weight of compound of formula I in such a portion. It will be appreciated that such concentrations may vary within wide limits, and it is possible that a concentrate of a compound of formula I could be formulated suitable for dilution to afford a "unit dosage form".

The present invention also includes a package containing preferably the above defined unit dosage forms in physical relation to instructions for administration of a therapeutically effective amount of a compound of formula I as a myotonolytic or muscle relaxant.

As indicated above the compounds may be administered orally in the form of tablets, powders, granules, capsules, suspensions, sirups and elixirs, or parenterally in the form of injectable solutions or suspensions. Aside from the compound of formula I the compositions may contain pharmaceutically inert organic or inorganic adjuvants, optionally granulating agents, binding agents, lubricants, dispersing agents, wetting agents and preservatives. Moreover, the pharmaceutical compositions may contain colouring, flavouring and sweetening substances, etc. Adjuvants for the production of tablets may be calcium carbonate, lactose, microcrystalline cellulose, mannitol, or talc. Starch and alginic acid or microcrystalline cellulose may be used as granulating and disintegrating agents, starch, polyvinylpyrrolidone and gelatine may be used as binding agents, and magnesium stearate, stearic acid, colloidal silicon dioxide and talc as lubricants. Tablet formulations may be coated or uncoated, with the coating being applied in a manner per se and having the purpose of delaying the disintegration and adsorption in the gastrointestinal tract, thus providing a retarded effect over a longer period. Suitable suspending agents for the production of liquid administration forms are especially methyl cellulose, tragacanth and sodium alginate. Suitable wetting agents are e.g. polyoxyethylene stearate and polyoxyethylene sorbitan-monooleate. Furthermore, preservatives such as p-hydroxy-benzoic acid alkyl ester may be used. Capsule formulations may contain the compound of formula I on its own or together with an inert solid diluent, for example calcium phosphate, starch, lactose, mannitol, colloidal silicon dioxide and microcrystalline cellulose.

Solid preparations are preferred, especially hard-filled capsules and tablets, for reasons of easier production and favourable administration.

The compounds may be administered in free base form or in pharmaceutically acceptable acid addition salt form. Such salt forms are known and include for example the hydrochloride. The free base forms and said acid addition salt forms exhibit the same order of activity.

"Alkyl, alkoxy or alkylthio" as used herein preferably refers to radicals containing up to 4 carbon atoms, especially 1 carbon atom.

The following Examples are illustrative of compositions for use in the invention.

EXAMPLE 1

Tablet Suitable for Oral Administration

Tablets containing the ingredients indicated below may be prepared by conventional techniques and are useful in treating spastic conditions at a dose of one or two tablets four times a day.

| Ingredient | Weight (mg) |
|---|---|
| 5-chloro-4-(2-imidazolin-2-yl-amino)-2,1,3-benzothiadiazole hydrochloride | 0.572 mg (≈0.5 mg base) |
| Lactose | 70.528 mg |
| Microcrystalline cellulose | 18.0 mg |
| Colloidal silicon dioxide | 0.45 mg |
| Magnesium stearate | 0.45 mg |
| | 90.0 mg |

If desired the tablet may be shaped so that it may be easily divided into two.

EXAMPLE 2

Capsule Suitable for Oral Administration

Capsules containing the ingredients indicated below may be prepared by conventional techniques and are useful in the treatment of spastic conditions at a dose of one capsule two to four times a day.

| Ingredient | Weight |
|---|---|
| 5-chloro-4-(2-imidazolin-2-yl-amino)-2,1,3-benzothiadiazole hydrochloride | 2.288 mg (≈2 mg base) |
| Lactose | 173.212 mg |
| Corn starch | 120.0 mg |
| Colloidal silicon dioxide | 1.5 mg |
| Magnesium stearate | 3.0 mg |
| | 300.0 mg |

EXAMPLE 3

Dragées Suitable for Oral Administration

Dragées containing the ingredients indicated below may be prepared by conventional techniques and are useful in the treatment of spastic conditions when administered at a dose of one dragée two to four times a day.

| Ingredient | Weight |
|---|---|
| 5-chloro-4-(2-imidazolin-2-yl-amino)-2,1,3-benzothiadiazole hydrochloride | 1.725 mg (≈1.5 mg base) |
| Polyvinylpyrrolidone | 3.6 mg |
| Lactose | 69.825 mg |
| Magnesium stearate | 0.9 mg |
| Colloidal silicon dioxide | 0.45 mg |
| Corn starch | 13.5 mg |
| Dragee mass | 100 mg |
| | 190 mg |

EXAMPLE 4

Sterile Solution for Injection

A solution for injection containing the ingredients indicated below may be prepared by convention techniques including buffering as indicated below and subsequent sterilizing in conventional manner. The solution may be injected once a day in the treatment of spastic conditions.

| Ingredient | Weight or Volume |
|---|---|
| 5-chloro-4-(2-imidazolin-2-yl-amino)-2,1,3-benzothiadiazole hydrochloride | 6.9 mg (≈6.0 mg base) |
| Sodium chloride | q.s. |
| Distilled water | to 5 ml |
| Buffer to pH 5 | |

If desired the solution may be sealed into ampoules.

EXAMPLE 5

Elixir for Oral Administration

An elixir containing the ingredients indicated below may be prepared by conventional techniques, including buffering as indicated below. The elixir may be administered once or twice a day in 2 ml quantities for the treatment of spastic conditions.

| Ingredient | Weight |
|---|---|
| 5-chloro-4-(2-imidazolin-2-yl-amino)-2,1,3-benzothiadiazole in free base form | 0.025 g |
| Glycerol | 10.0 g |
| Tinctura Auranti dulcis | 10.0 g |
| Saccharin | 0.02 g |
| Karion F | 60.0 g |
| Caramel-Sugar colouring | 0.05 g |
| Ethyl alcohol pharm. | 15.0 g |
| Citric acid to pH 5 | q.s. |
| Dist. water | 100.0 ml |

We claim:

1. A method of treating spastic conditions which comprises administering to an animal in need of such treatment a therapeutically effective amount of a compound of the formula

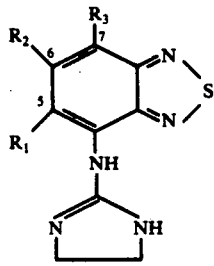

wherein each of $R_1$, $R_2$ and $R_3$ independently, is hydrogen, halogen, alkyl, alkoxy, nitro, cyano, hydroxy or alkylthio,
or a pharmaceutically acceptable acid addition salt form thereof.

2. A method of claim 1, wherein the compound is 5-chloro-4-(2-imidazolin-2-ylamino)-2,1,3-benzothiadiazole.

3. A method of claim 2, wherein the compound is administered at a daily dose from about 0.001 to about 1 mg/kg animal body weight of compound when calculated on the free base form.

4. A method of claim 3, wherein the compound is administered at a total daily dosage of from about 1 to about 10 mg of the compound when calculated on the free base form.

5. A method of claim 4, wherein the compound is administered two to four times a day in the form of a solid unit dosage form containing from about 0.25 to about 1.8 mg of the compound when calculated on the free base form.

6. A method of claim 1, wherein the compound is administered at a daily dose from about 0.001 to about 1 mg/kg animal body weight of compound when calculated on the free base form.

7. A method of claim 1, wherein the compound is administered at a total daily dosage of from about 1 to about 10 mg of the compound when calculated on the free base form.

8. A method of claim 1, wherein the compound is administered two to four times a day in the form of a solid unit dosage form containing from about 0.25 to about 2.0 mg of the compound when calculated on the free base form.

9. A method of relaxing muscles which comprises administering to an animal in need of such treatment a muscle-relaxing amount of a compound of the formula

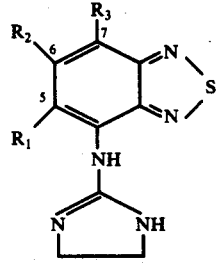

wherein each of $R_1$, $R_2$ and $R_3$ independently, is hydrogen, halogen, alkyl, alkoxy, nitro, cyano, hydroxy or alkylthio,
or a pharmaceutically acceptable acid addition salt form thereof.

10. A method of claim 9, wherein the compound is 5-chloro-4-(2-imidazolin-2-ylamino)-2,1,3-benzothiadiazole.

11. A method of claim 10, wherein the compound is administered at a daily dose from about 0.001 to about 1 mg/kg animal body weight of compound when calculated on the free base form.

12. A method of claim 5, wherein the compound is administered at a total daily dosage of from about 1 to about 10 mg of the compound when calculated on the free base form.

13. A method of claim 12, wherein the compound is administered two to four times a day in the form of a solid unit dosage form containing from about 0.25 to about 1.8 mg of the compound when calculated on the free base form.

14. A method of claim 9, wherein the compound is administered at a daily dose from about 0.001 to about 1 mg/kg animal body weight of compound when calculated on the free base form.

15. A method of claim 11, wherein the compound is administered at a total daily dosage of from about 1 to about 10 mg of the compound when calculated on the free base form.

16. A method of claim 9, wherein the compound is administered two to four times a day in the form of a solid unit dosage form containing from about 0.25 to about 2.0 mg of the compound when calculated on the free base form.

* * * * *